United States Patent [19]

Goldfield

[11] Patent Number: 6,033,367
[45] Date of Patent: Mar. 7, 2000

[54] SMART BOTTLE AND SYSTEM FOR NEONATAL NURSING DEVELOPMENT

[75] Inventor: Eugene C. Goldfield, North Stonington, Conn.

[73] Assignee: Children's Medical Center Corporation, Boston, Mass.

[21] Appl. No.: 09/132,015

[22] Filed: Aug. 10, 1998

[51] Int. Cl.$^7$ .................................................. A61M 15/00
[52] U.S. Cl. .......................... 600/529; 600/532; 215/11.1; 606/234; 606/236; 73/23.3
[58] Field of Search .................................... 600/529, 538; 215/11.1–11.6; 606/234–6; 73/23.3; 422/84

[56] References Cited

U.S. PATENT DOCUMENTS

| | | | |
|---|---|---|---|
| 3,790,016 | 2/1974 | Kron ....................................... | 215/11.1 |
| 3,895,533 | 7/1975 | Steier ....................................... | 600/590 |
| 4,232,687 | 11/1980 | Anderson-Shanklin ................ | 600/590 |
| 4,475,559 | 10/1984 | Horn ....................................... | 128/716 |
| 4,586,621 | 5/1986 | Dahan ................................... | 215/11 R |
| 4,669,461 | 6/1987 | Battaglia et al. ................... | 128/202.15 |
| 4,966,580 | 10/1990 | Turner et al. ......................... | 215/11.4 |
| 5,078,733 | 1/1992 | Eveleigh et al. ........................ | 606/236 |
| 5,830,235 | 11/1998 | Standley ................................. | 606/236 |
| 5,904,140 | 5/1999 | McGoogan .......................... | 128/200.24 |

OTHER PUBLICATIONS

Donald S. Finan and Steven M. Barlow "The Actifier: A Device for Neurophysiological Studies of Orofacial Control in Human Infants", Journal of Speech and Hearing Research, vol. 39, 833–838, Aug. 1996.

*Primary Examiner*—Robert L. Nasser
*Attorney, Agent, or Firm*—Nutter, McClennen & Fish, LLP

[57] ABSTRACT

A system for diagnosing or monitoring sucking/swallowing/breathing competence of an impaired neonate or post-operative infant, wherein a processor receives a sensed signal from a breath sensor, and develops an output for intraoral tactile or flow control feedback. In a feeding or monitoring embodiment, the processor applies the signal to control a liquid feeding valve which supplies nutrients through a feeding nipple. In various control regimens, the processor acts as a safety device and operates to restrict or close the valve to reduce flow when slowing or cessation of breath is detected, or acts as a training device to set or pace, or initially to develop basic competence, at an appropriate rate. In further embodiments, the processor also receives a signal from an intraoral suction transducer or muscle pressure gauge, and operates to control flow to a level appropriate to the available sucking activity, or to change the level to maintain a stable and non-slowing breath rate. In another embodiment specifically adapted for manual feeding, monitoring or intervention, the processor displays a waveform indicative of the breath or air flow sensor output, and a manually operated pressure bulb is provided to allow a nurse or care giver to apply a rhythmic muscular pressure stimulus via a feeding or surrogate nipple in a manner visually synchronized with the displayed breath activity. Preferred frequencies and phased coordination with the breath cycle may facilitate the development of competence and the coordination or linkage of the three sensorimotor areas. The system may also provide medical records of sensed events, and trigger an alarm when it detects a dangerous condition.

14 Claims, 3 Drawing Sheets

SMART BOTTLE AND SYSTEM FOR NEONATAL NURSING DEVELOPMENT

CROSS-REFERENCE TO RELATED APPLICATIONS

Not applicable.

STATEMENTS REGARDING FEDERALLY SPONSORED RESEARCH

Not applicable.

BACKGROUND OF THE INVENTION

The present invention relates to neonatal development, and more particularly to the development and coordination of sucking, swallowing and breathing abilities. While the neurological and tissue development for these biological activities generally occurs early in fetal development, it is still relatively common for extremely premature or low birth weight infants to enter the world with no suckling reflex, poorly developed breathing ability, and possibly other neurological deficits requiring that they be maintained on various support systems including cardiac, breath and feeding systems for the first weeks of their lives. Under these circumstances, feeding is initially effected by direct nasal intubation to the intestine.

The transition from tube feeding to breast or bottle feeding requires the development of the ability to suck and also to coordinate sucking with swallowing and breathing. Low birthweight neonates as well as newborn cardiac surgery patients making this transition often exhibit feeding apnea during which nasal airflow ceases entirely for a period of several seconds. This apnea may result from excess milk flow, from lack of coordination between swallowing and breathing, or from repeated swallowing. The degree of difficulty in making the transition from tube feeding to bottle feeding may be compounded by the presence of apnea of prematurity, as well as by other factors. These difficulties may necessitate continuous monitoring, prolonging the time interval that the neonate remains in the intensive care or transitional care unit.

Numerous researchers have investigated the development of sensorimotor pathways and developmental factors responsible for activity of the perioral region, and a number of sensing techniques for evaluating or diagnosing deficits of muscular activity or nerve activation in that area have been developed. In addition, a range of practical devices such as pacifiers have been suggested or promoted for enhancing the development or increasing the functional ability of an infant's nursing. However, these generally rely on the presence of a threshold level of sucking competence. Initially, for the above-mentioned classes of infants, such competence is absent, and the transition to bottle or breast feeding is therefore a critical one which can require full-time observation and close attention by a nurse/monitor during feeding.

Sucking behavior is believed to depend both on control of a neuronal network located in the brain stem reticular formation, as well as on afferent feedback of nerve signals from the facial and mouth tissues. Observations on healthy infants have identified several patterns of sucking, and have commonly also noted the infants ability to change the nature or type of sucking activity based on the presence or absence of liquid nutrients. Furthermore, certain natural frequencies of sucking activity closely related to the breathing cycle have also been identified in a range of normal sucking behavior. These observations of a temporal coordination or phase relationship of breathing and sucking suggest the involvement of related neuronal systems. More recently, Finan and Barlow, in J. Speech and Hearing Res. 39:833–839 (August, 1996) have suggested the use of an instrument which they call an actifier, to alter the sucking response by operating as a stimulus within the frequency band of normal sucking movement. The device applies a periodic pressure pulse to the nipple of a pacifier, and measures muscular responses in the mouth of the infant. The actifier of those researchers essentially was used to investigate responsiveness of the sucking neuronal control to cyclic mechanical stimulation of the intraoral tissue in normal full term human infants and neonates. Substantial questions remain as to whether such stimulation would produce similar results in very low birth weight or post operative cardiac neonates, as well as their ability to respond to such stimuli, and whether such stimulation may have any effect on the initial development of, or the mechanisms by which, competence is acquired.

Accordingly, there remains a need for a device for diagnosing or managing or training neonatal sucking and feeding deficits during the transition from feed tube intubation to autonomous feeding.

There is also a need for a device that reduces the degree of individualneed for, or the demands placed upon, a human monitor during the time a neonate makes the transition to natural feeding.

BRIEF SUMMARY OF THE INVENTION

One or more of these needs are addressed in accordance with a basic embodiment of the present invention by providing a system wherein a processor receives a sensed signal from at least one sensor, which is preferably a breath expiratory flow sensor, and develops an output for controlling a sucking object such as a pacifier or feeding nipple. In one embodiment, adapted for automated feeding and monitoring of a neonate, a microprocessor receives a first signal from a breath flow sensor, and applies the signal to a liquid feeding valve which controls the supply of nutrients through a feeding nipple. In various control regimens, the processor acts as a coordination controller and operates to close the valve or to reduce flow when a slowing or cessation of breath is detected. Preferably the processor also receives a pressure signal from an intraoral suction sensor and/or muscle strain gauge, and it operates to control flow to a level demanded by or appropriate to the detected muscular or sucking activity, or it changes the level to maintain a stable and non-slowing breath rate. In another embodiment specifically adapted for manual feeding, monitoring or intervention, the processor displays a waveform indicative of the air flow sensor output, and a manually operated pressure bulb is provided to allow a nurse or care giver to apply a tactile pressure stimulus to the nipple in a manner visually synchronized with the displayed breath activity. For example, the pressure bulb may be used to produce pulsation at a frequency of approximately two Hz in phase relation to the observed breathing cycles to induce a sucking response, or to entrain the sucking to an appropriate rate. This embodiment may also include an intraoral pressure sensor, in which case, the processor preferably also displays the measured oral suction or muscle tension as a graph on the same display as the breath measurement display. By jointly displaying the breathing and sucking signals the nurse or other monitor may quickly identify their phase relation and operate the hand held pressure bulb as a reinforcing pressure stimulus.

In yet a further aspect of the first embodiment described above, the system may operate as an automated feeding mechanism in which a pressurized supply of milk or formula is provided to a valved nipple under control of the processor. Thus, the device may operate as a pressure assisted feeding unit synchronized with the breath airflow to promote development of swallowing competence. The valve is also controlled to limit the amount of fluid delivered in accordance with slowing or adverse changes in the respiratory airflow, thus further acting as a safety monitor. In accordance with a further aspect of the first embodiment of the invention described above, the system may in different embodiments, measure orally applied pressure or suction level, or may also apply a stimulus, using one or separate transducing elements. For example, the system may include a suction sensor for detecting suction level, a pressure transducer for detecting muscular pressure exerted by the tongue or lips, and may include a pressure applying element, such as a valved supply of pressurized fluid connected to pulsate a closed chamber in the nipple for producing a tactile sensory stimulation when actuated. In accordance with this aspect fo the invention, the controller controls the pressure or degree of valve opening of the nutrient supply in accordance with the sensed magnitude of the sucking activity as well as within the limits dictated by breath timing or adverse slowing of activity, and may also apply sensory stimulation via the pressure actuator in coordination with the timing of the sensed oral activity. In the latter case, the device acts as a direct sensory feedback loop to stimulate sensorimotor activities and train sucking behavior.

BRIEF DESCRIPTION OF THE DRAWINGS

The foregoing features of this invention, as well as the invention itself, may be more fully understood from the following description of several illustrative embodiments and the drawings, in which.

DETAILED DESCRIPTION OF THE INVENTION

Figure 1:
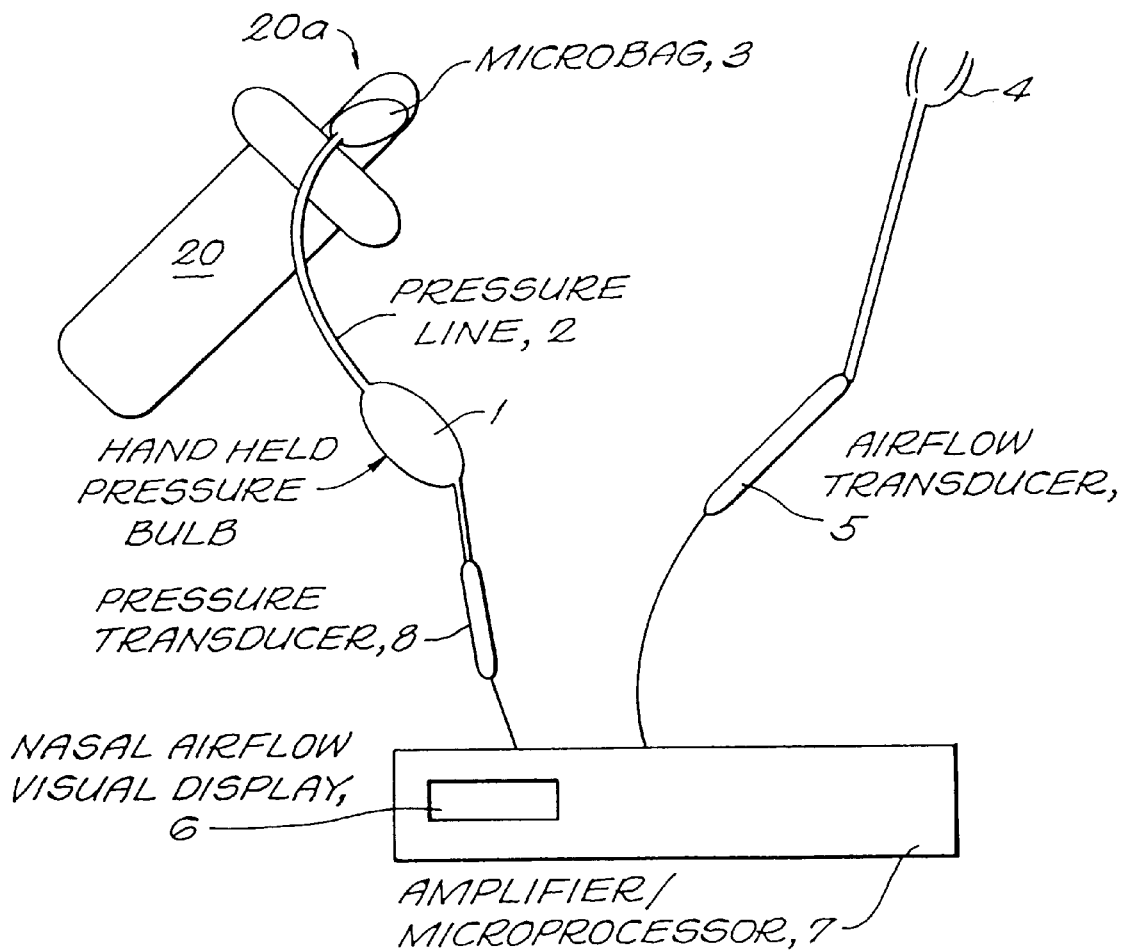
FIG. 1 illustrates a basic embodiment of the invention useful for assisting the manual feeding or evaluation of neonates.

FIG. 1 illustrates a simplified embodiment of the invention having application primarily to manual feeding or evaluation of a neonate suffering from poorly developed or impaired sucking capabilities. As shown, the system includes a respiratory airflow transducer assembly 4, 5 which is connected to a processor or controller 7 that receives and processes the signal from the airflow transducer. In a typical embodiment, the air flow transducer 5 is a simple warm air detector such as a thermistor type transducer that has a fast response and is mounted near the nostril or in a special chamber or cap 4 fitted over the nostril to detect exhalation. In general, it is contemplated that the signal produced by the transducer 5 will be converted to a detection signal which will vary in voltage, resistance, current or similar electrical characteristic, and which is sampled at a rate sufficient to smooth the signal output and generate a pattern, such as a waveform or rising signal graph which indicates the timing of each exhalation. This latter processed signal is then displayed on a display 6 such as a simple LED bar or line graph, or other intuitively interpretable display.

As further shown in FIG. 1, this embodiment of the system includes a pressure bulb 1 which may be held in the hand and squeezed to produce a pressure pulse or pressurized condition in a pressure line 2. Pressure bulb 1 is connected via the pressure line 2 to a microbag 3 which, as illustrated, fits within the nipple portion 20a of a nursing device 20. The nursing device 20 may be a fluid filled nursing bottle as described more fully below in connection with FIG. 2, or may be a closed surrogate device such as a pacifier. In any event, the pressure line 2 is connected to a microbag 3 within the nipple portion so that creation of pressure via the hand held bulb 1 inflates the microbag and exerts a gentle pressure or strain within the nipple portion. Pressure bulb 1 is also connected via a separate pressure line (not numbered) or via the same pressure line 2, to a pressure sensor 8 which indicates the level of exerted pressure. In further embodiments, multiple lines may be connected to one or more additional pressure transducers (for example, also to a muscle pressure indicator or a suction indicator when it is desired to further indicate the intraoral pressure or suction). The output of the sensor 8 and any additional transducer is also provided to the control processor 7, which visually displays both the prevailing or applied pressure and the air flow transducer output.

An additional transducer is a swallow detector such as a microphone or piezo sensor for developing information for display, alarm, or control purposes.

In use, the nurse or parent monitoring an infant who is feeding or simply sucking a pacifier, observes the nasal airflow visual display and squeezes the pressure bulb 1 to inflate the microbag inside the nipple, thus applying a pressure pulse against the lips of the infant. The pressure change inside the bulb that is produced with each squeeze is transduced as an electrical signal and appears as a display on the control processor unit 7 so that both the oral stimulus and breath waveform appear together.

In operation according to one basic protocol of the invention, the task for the nurse or parent is to squeeze the bulb such that each squeeze is synchronized with the infant's nasal airflow signal. This provides a coordination of afferent nerve signals for sucking and breathing for the infant. As the infant begins to acquire sucking competence, the pressure bulb is squeezed at a progressively advanced rate to increase the speed of the infant's sucking rate so that it approaches approximately two sucks per second and approximately two sucks for each breath. Applicant has found this particular ratio to be optimal for coordination of sucking and breathing to occur in a tested sample of infants.

In addition to providing an intraoral tactile feedback to promote a sucking activity similar to the non-nutritive sucking behavior, e.g. like thumb-sucking or pacifier sucking in a normal infant, the preceding elements may be attached to an actual milk or nutrient bottle which has been specially fitted with additional elements to actively supply a controlled flow of nutrient. This embodiment is used to teach nursing behavior.

In this case, the bottle 20 of FIG. 1 preferably includes the further element of a nipple control valve 37 (FIG. 2) which is operated by the control processor 7, and the bottle preferably also includes a mechanism for applying pressure to or otherwise positively expelling nutrient from the bottle, such as a pump or pressure applying servo or piston mechanism as described further below. The nutrient may be supplied from a reservoir within the bottle, such as a plastic bag, which is placed under pressure to feed nutrient to the regulator or control valve 37 during a second mode of operation which applicant denotes simply as nutritive feeding.

Figure 2:
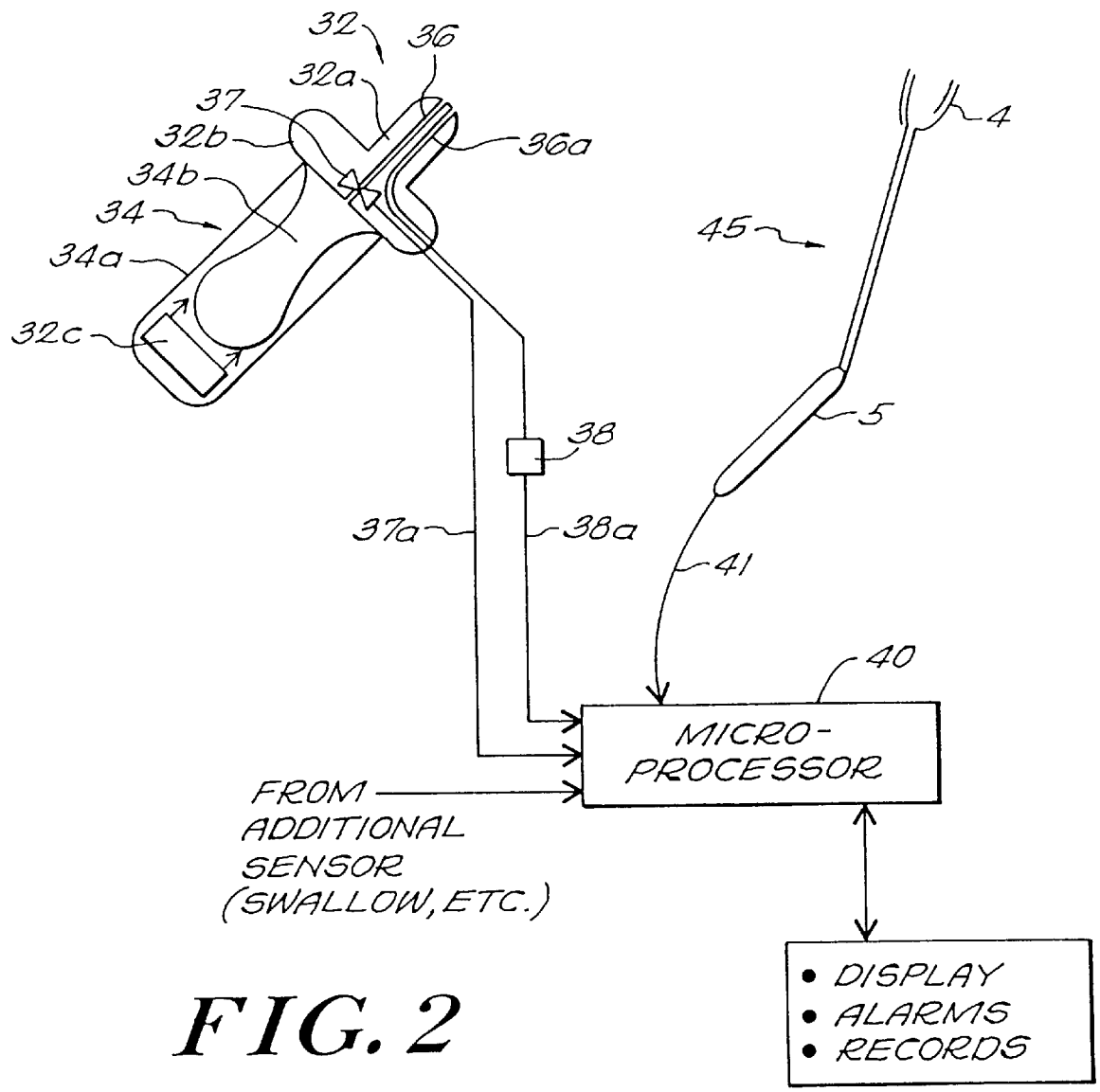
FIG. 2 illustrates another embodiment of the invention for automated nursing and control.

General aspects of this form of operation will be better understood from the following brief description coupled with discussion of a representative set of operating protocols for training, control or monitoring with the device shown in FIG. 2.

In this embodiment of a system 50, a more complex feed assembly 30 operates in conjunction with a processor 40 and breath sensor 45 to effect feeding, training and monitoring. The breath sensor 45 may include a breathing cup or other mounting assembly 4 and a transducer 5 as in the embodiment of FIG. 1, which provides a signal along line 41 to the processor 40. The feed assembly 30 on the other hand is both a controlled feeding source and a sensing unit, connected to both accept control signals from and provide sensor signals to the processor 40. For ease of understanding, the feed assembly 30 is illustrated as a modified nursing bottle, and its various active supply or sensing components will be described in the context of such a modification. However, it will be better appreciated following the detailed description below, that its operative structure may be reduced to a specialized nipple assembly and a feed supply line connected to the nipple, so that practical embodiments may have a shape quite different from that of a bottle, and may appear more like a simple supply tube with a nipple ending. This structure is well adapted to implementation in diverse neonatal ergometric embodiments, having features smaller than a conventional bottle, differently shaped, and more readily held. As schematically shown in FIG. 2, the feed assembly 30 includes a nipple or oral feed portion 32 and a bottle or feed supply portion 34. Illustratively, the feed supply portion 34 is formed of a semirigid outer housing 34a, a collapsible nutrient pouch 34b, and a pressure drive unit 34c. These three elements cooperate to provide a pressurized supply of milk or formula to the oral feed portion 32.

The nipple or oral feed assembly 32 is shaped with a first portion 32a that fits within the neonate's mouth, and a rim or wider portion 32b that forms a pressure surface or stop to prevent over-insertion of portion 32a.

Within the buccal or oral feeding part 32a, a feed passage which is preferably a tube 36 centrally extends from the feed supply portion 34 to the tip, and a feed control valve 37 is positioned to restrict or close the passage 36 upon activation via control signal line 37a from the control processor 40. A second passage 36a within the tip leads to a lead-out tube attached to a suction sensor 38, providing an indication of the detected intraoral suction along line 38a to the processor. Thus, the processor receives signals from the breath flow sensor and the suction sensor, and controls valved flow to the milk line 36. While not specifically illustrated, the invention further contemplates that additional determinations may also be either provided to the processor as sensing signals, or derived by the processor from the above enumerated signals. Thus, for example, a milk flow rate sensor may be provided, or flow may be determined from data such as the setting of valve 37 and the feed pressure, using a formula or stored table. Also, a strain gauge may be provided within the nipple portion 32 to produce a signal indicative of muscular pressure.

In general, the microprocessor of FIG. 2 is configured to not only receive and process sucking and breathing patterns, although it may include a display as shown in FIG. 1, but is also programmed to implement diagnostic or control functions. These are of three types, general features of which are described below in connection with the operational chart of FIG. 3, which illustrates a moderately versatile embodiment of the invention operable in all three modes.

Figure 3:
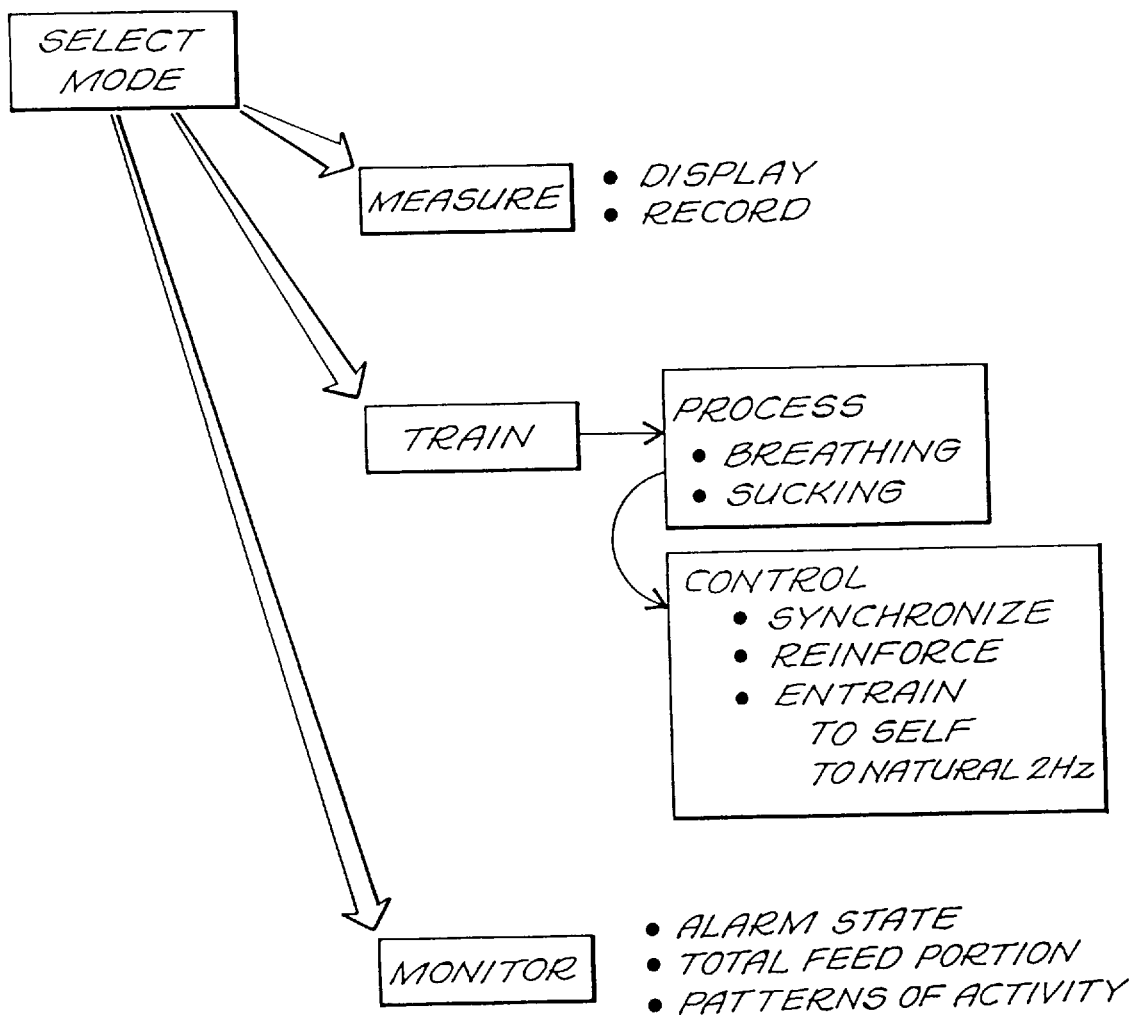
FIG. 3 illustrates operation of the invention.

As shown in FIG. 3, the system processor operates in three modes, denoted the measuring, training and monitoring modes. These correspond roughly to development stages or needs of the neonate. The measuring mode is essentially a programmed signal processing mode, in which the processor detects the sensor signals, and operates to display or record in graphic or numerical form the breath signal, the intraoral sucking activity signal, and possibly secondary information derived from these signals, such as their phase relationship or times or intervals of disruption or slowing. This mode is of use for baseline and diagnostic assessment, and most of its processing is employed for the other modes described below.

The second mode, denoted the training mode, is characterized by the microprocessor further producing control signals to influence or attempt to influence sucking behavior. Thus, it may actuate a non-feeding pressure pulse, i.e., a tactile stimulus, in a manner analogous to the nurse-operated system of FIG. 1, and synchronize the pulse to the breathing cycle, or it may control the opening of the feed valve 37. In each case, the invention contemplates that the processor operate in a programmed mode to either make a diagnostic determination—e.g. that the neonate lacks the ability to perform or to coordinate sucking activity, as evidenced by the output of sensor 38, or else operates to train the neonate's activity. In this mode, the system is useful for making basic determinations of the patient's developmental achievement, and for training the detected sucking once this is developmentally feasible. The second mode thus relies on the basic sensor signal processing of the first mode, and adds control, training and evaluation modules.

Finally, the preferred implementation of the system operates in a third mode as a monitor, which may for example monitor for alarm conditions such as apnea during feeding, or monitor the quantity of fluid ingested at each feeding.

In this context, the processor implements a control program (for example to adjust feed rate, or to present a tactile stimulation, with a timing to entrain the sucking/breath complex to a stable period), or actuates an alarm (for example if apnea is detected, or the entrainment protocol proves ineffective to maintain the rates within a safe band.

In each of these modes, the processor is preferably equipped with a data sorting program which recognizes "events", and a storage program which forms records of the identified events, thus creating a medical record of the sensed observable conditions. One such observable is the existence of sucking behavior, which is identified as the attainment of a threshold suction level at sensor 38, and/or a periodic variation therein, as detected in the first mode of operation. Another is the level of sucking coordination, which may be defined by a formulaic measure, such as the degree of overlap with a step function given by half the breathing period. Still other "events" or measures may include the occurrence or near-occurrence of apnea, or another measured deviation from an established pattern. Each of these events is readily defined by simple formulae and processing instructions operable on the outputs of the sensors illustrated in FIG. 2, and their detection may be implemented with an inexpensive control microprocessing chip. In one embodiment, once events are determined, they are output in graphical form, to provide records similar to EKG charts quickly illustrating the detected pattern or relationship. It will be understood, however, that a device in accordance with the present invention need not possess all of the above features. Indeed, a basic embodiment of great practical utility may have no recording or output capabilities, but be embodied as a "smart bottle" which operates a flow restrictor in accordance with a simple control program to bring sucking into synchronization with the breathing cycle, and/or to cut off when an apnea-like condition or an over-feeding condition is detected.

Thus, the invention provides a range of constructions useful for accurately determining or managing the relationship between the different coordinated events of neonatal nursing activity, and for safely monitoring or training such activity. The necessary sensors may be implemented with small components, and actuators such as valves or strain transducers may be integrated into a nipple assembly, for example as embedded piezoelectric bimorphs, to provide a hardy device free of protruding hardware, that operates at a safe voltage level.

Having thus described several representative and preferred embodiments of the invention, further variations and modifications will occur to one of ordinary skill in the art, and all such variations and modifications are considered to be within the scope of the invention, as described herein and set forth in the claims appended hereto.

What is claimed is:

1. A training system for use by a neonate having a sensorimotor deficit of breathing/swallowing/sucking competence, such system comprising a breath sensor for developing a signal indicative of breathing a processor which processes the signal to form an indication of breathing cycle, and a feedback system connected to an intraoral nursing device, configured for applying feedback to the device in coordination with the breathing cycle.

2. A training system according to claim 1, wherein the feedback system includes a pressurized feed source, and a valve, said valve being controlled by said processor to limit feeding of nutrient in coordination with said breathing cycle.

3. A training system according to claim 1, wherein the feedback system includes a manually controlled pressure source connected for applying a tactile intraoral pressure pulse in accordance with the breathing cycle.

4. A training system according to claim 3, wherein the processor causes the breathing cycle to be displayed, whereby said tactile pressure pulse may be coordinated by manual control while observing the displayed breathing cycle.

5. A training system according to claim 1, wherein the processor applies a control signal to drive said pressure pulse at a rate of approximately two Hz.

6. A training system according to claim 5, further comprising an intraoral pressure sensor for sensing oral sensorimotor activity of the neonate, and wherein the processor receives a signal from the intraoral pressure sensor and applies pressure in accordance with said signal.

7. A training system according to claim 6, wherein the processor progressively changes timing of applying said pressure so as to train a sucking response into rhythmic coordination with detected breathing.

8. A training system according to claim 6, wherein the processor progressively changes timing of applying said pressure so as to train a sucking response having a regular period in the range of 1–3 Hz.

9. A training system according to claim 1, wherein the processor includes means for recognizing events and for storing records indicative thereof.

10. A training system according to claim 1, wherein the processor includes means for recognizing alarm events and for providing an alarm signal indicative thereof.

11. A nursing device comprising:

a feed bottle having a feed nipple a breath sensor, and a controller which receives a signal from the breath sensor and controls the feed nipple in accordance therewith.

12. A nursing device according to claim 11, wherein the controller operates to close the nipple when the breath sensor indicates apnea.

13. A nursing device according to claim 11, wherein the controller adjusts a feed valve to synchronize sucking with breathing detected by the breath sensor.

14. A nursing device according to claim 11, wherein the controller controls a feed valve to maintain a stable breath rate during nursing.

* * * * *